(12) United States Patent  
Berkcan et al.

(10) Patent No.: US 7,696,676 B2  
(45) Date of Patent: Apr. 13, 2010

(54) PIEZOELECTRIC COMPOSITE APPARATUS AND RELATED METHODS

(75) Inventors: Ertugrul Berkcan, Clifton Park, NY (US); Emad Andarawis Andarawis, Ballston Lake, NY (US); Robert John Wojnarowski, Ballston Lake, NY (US); Charles Scott Sealing, Clifton Park, NY (US); Charles Erklin Seeley, Niskayuna, NY (US); Eladio Clemente Delgado, Burnt Hills, NY (US); David Cecil Hays, Niskayuna, NY (US); Christopher James Kapusta, Delanson, NY (US); Nanette Judith Gruber, Clifton Park, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 616 days.

(21) Appl. No.: 11/640,803

(22) Filed: Dec. 18, 2006

(65) Prior Publication Data

US 2008/0143216 A1 Jun. 19, 2008

(51) Int. Cl.  
*H01L 41/08* (2006.01)

(52) U.S. Cl. ........................ 310/364; 310/365; 310/366

(58) Field of Classification Search .......... 310/363–366  
See application file for complete search history.

(56) References Cited

U.S. PATENT DOCUMENTS

| 4,623,813 | A |   | 11/1986 | Naito |
| 4,726,099 | A |   | 2/1988 | Card et al. |
| 4,964,145 | A |   | 10/1990 | Maldonado |
| 5,184,516 | A | * | 2/1993 | Blazic et al. .................. 73/799 |
| 5,189,914 | A |   | 3/1993 | White |
| 5,615,466 | A |   | 4/1997 | Safari et al. |
| 5,818,150 | A |   | 10/1998 | Yamamoto |
| 5,873,154 | A |   | 2/1999 | Ylilammi et al. |
| 6,060,819 | A |   | 5/2000 | Tagami et al. |

(Continued)

FOREIGN PATENT DOCUMENTS

JP          2000065578 A    *  3/2000

(Continued)

OTHER PUBLICATIONS

DARIO; Touch-sensitive polymer skin uses piezoelectric properties to recognize orientation of objects; Sensor Review, Oct. 1982.

(Continued)

*Primary Examiner*—J. SanMartin  
(74) *Attorney, Agent, or Firm*—Bracewell & Giuliani LLP (57) ABSTRACT

A piezoelectric planar composite apparatus to provide health monitoring of a structure and associated methods are provided. The piezoelectric planar composite apparatus includes a piezoelectric electric material layer, multiple electrodes positioned in electrical contact with the piezoelectric material layer, and multiple sets of electrode interconnect conductors each positioned in electrical contact with a different subset of the electrodes and positioned to form multiple complementary electrode patterns. Each of the complementary electrode patterns is positioned to form an electric field having an electric field axis oriented along a different physical axis from that of an electric field formed by at least one other of the complementary electrode patterns. The interconnect conductors can be distributed over several electrode interconnect conductor carrying layers to enhance formation of the different complementary electrode patterns.

22 Claims, 9 Drawing Sheets

U.S. PATENT DOCUMENTS

| | | | |
|---|---|---|---|
| 6,620,287 | B2 | 9/2003 | Cass |
| 6,629,341 | B2 | 10/2003 | Wilkie et al. |
| 6,781,285 | B1 | 8/2004 | Lazarus et al. |
| 6,964,201 | B2 * | 11/2005 | Xu et al. ................ 73/794 |
| 2002/0073781 | A1 | 6/2002 | Hashimoto |
| 2004/0040132 | A1 | 3/2004 | Wilkie et al. |
| 2006/0197415 | A1 * | 9/2006 | Nakashio et al. ............ 310/365 |
| 2008/0289426 | A1 * | 11/2008 | Kearns et al. ................ 73/632 |

FOREIGN PATENT DOCUMENTS

WO     WO 01/33648 A1     5/2001

OTHER PUBLICATIONS

Article titled Piezoelectric Fibers with Metal Core, National Institute of Advanced Industrial Science and Technology (AIST), found at http://unit.aist.go.jp/smart/eg/pmt/pmt-2/purpose.html.

R. Bryant, et al., presentation "Radial Field Piezoelectric Diaphragms," Nasa Langley Research Center, 2002.

W Wilkie, et al., "Low-Cost Piezocomposite Actuator for Structural Control Applications," presented at SPIE's 7th Annual International Symposium on Smart Structures and Materials, Newport Beach, CA, Mar. 5-9, 2000.

Azzouz et al., "Finite Element Modeling of MFC/AFC Actuators and Performance of MFC," Journal of Intelligent Material Systems and Structures, vol. 12—Sep. 2001.

Advanced Cerametrics, Inc., "Piezoelectric Ceramic Fiber Composites," found www.aci-tech.com/piezo_fiber.html.

W Wilkie, et al., Recent Developments in NASA Piezoelectric Actuator Technology, undated.

S.J. Shaw et al., article "Adhesive Bonding in Severe Environments—Epoxy Bismaleimide Based Adhesives," found at www.azom.com/details.asp? Article ID=354.

Webpage; "Scanning Acoustic Microscope Service," Materials Resources International (MRI), found at www.materialsresources.com/sam/sam.htm.

Web page, "Sonoscan Is a Leading Worldwide Provider of Acoustic Microscope Instruments," 2005 Sonoscan, Inc., found at www.sonoscan.com.

H.A. Sodano, thesis, "Macro-Fiber Composites for Sensing, Actuation and Power Generation," Jul. 28, 2003, found at www.scholar.lib.vt.edu/theses/available/etd-08012003-105114/.

Powerpoint slides, "Free-Strain Measurement Methodology for the NASA MFC," Mesurements Group, Inc., Raleigh, NC.

Powerpoint slides of innovative actuator, NASA Langley Research Center, found at www.rti.org/page.cfm?objectid=89A85300-43F1-4006-AE2C8A707E5FDC6E.

* cited by examiner

PIEZOELECTRIC COMPOSITE APPARATUS AND RELATED METHODS

BACKGROUND OF THE INVENTION

1. Field of the Invention

The present invention relates generally to sensors and actuators. More specifically, the present invention relates to piezoelectric composite apparatus and related methods of manufacture and use.

2. Description of the Related Art

Various types of platforms such as, for example, aircraft structural components, aircraft skins, or other related components, when in operation, are subjected to various environmental conditions such as stress and strain, exposure to temperature extremes, and significant vibration energy. Due to the various environmental conditions, such components can suffer material degradation over time.

Structural health monitoring helps promote realization of the full potential of such components. Remotely positioned sensors have been installed adjacent to, placed on, or embedded within such structures/components to monitor various parameters such as, for example, strain levels, stress, temperature, pressure, or vibration level to help manage physical inspection schedules, maintenance schedules, to help predict material failure, and generally monitor the "health" of such components.

Such sensors have been made using a composite material which can generate small electrical currents when the material is deflected, such as when the monitored component is subjected to a stress or strain. Piezoelectric material is but one example of materials that can perform this function. As a stress or strain is applied to the structure being monitored, the body of the sensor deforms or deflects, causing the piezoelectric material to convert a fraction of the mechanical energy of the stress or strain to electrical energy.

Conventional piezoelectric sensors are typically manufactured using a layer of piezoelectric material positioned between either planar or interdigitated electrodes made of, for example, copper, gold, etc., or combination thereof, and positioned in either direct or indirect contact with the piezoelectric material to form a relatively thin laminate. One methodology of forming the sensor includes using piezoelectric fiber composite material. Such piezoelectric material can be made by a process which includes bonding together relatively thin piezoelectric wafers using a liquid epoxy to form a stack, bonding the stack using a relatively moderate pressure and temperature, and slicing the stack to form multiple sheets of piezoelectric fiber composite material having each strand of the piezoelectric material separated by the epoxy.

The sensors can be attached to or embedded within various structures, without damage, to be monitored using, for example, a graphite epoxy composite which can withstand temperatures of up to approximately 150° C. to 160° C. Depending upon the conductive properties of the material to be monitored or of the material used to connect the sensor to the material to be monitored, an insulator such as glass epoxy or a polyimide such as Kaplon® manufactured by DuPont® can be used.

Completed sensors and other apparatus manufactured using conventional piezoelectric composite methodologies and materials have not been able to be embedded within materials such as, for example, carbon or carbon fiber composites, which are subjected to high pressures and high composite laminating temperatures, as part of their own manufacturing, or extreme pressures and temperatures when in operation. Recognized by the inventors is the need to utilize bonding materials, both within the structure of the sensor and to connect the sensor to the structure to be monitored, that are capable of withstanding high-pressure and high temperature such as those present when the sensors are used in structures subjected to high pressures and high temperatures as part of their own manufacturing and sensor embedding process or in operation.

Regardless of the material composition of the structure to be monitored, installation of the sensors adjacent to or within the structure to be monitored has required the user to first determine the orientation of usable or expected strain or other health indicator and then position the sensors so that the electric field generated by the piezoelectric material-electrode combination would be at least somewhat oriented along the axis associated with the health indication. Recognized by the inventors is that this determination cannot always be readily made because the axis of the usable strain can vary over time. Further, recognized by the inventors is that even if the axis of usable strain were fixed in time, the sensors may not always be properly positioned and can often not be properly nondestructively re-positioned, especially where the sensors are embedded within the structure to be monitored. Thus, recognized is the need for a piezoelectric apparatus which can be readily adapted to align the axis of the sensor, electric field with the axis of usable strain to enhance energy transfer.

SUMMARY OF THE INVENTION

In view of the foregoing, embodiments of the present invention advantageously provide a piezoelectric planar composite apparatus including piezoelectric material such as, for example, PZT or PZT fibers, which can be embedded, aligned, and mechanically and electrically connected to form a durable sensor based on piezoelectric and/or other similar technologies. According to embodiments of the present invention, the piezoelectric planar composite apparatus includes a plurality of layers of insulating material which carry electrode interconnect conductors electrically interconnected to electrodes which are, in turn, in electrical communication with the piezoelectric material, to produce electrical signals in response to mechanical inputs, to thereby provide for monitoring various health-related parameters such as, for example, strain levels, stress, temperature, pressure, or vibration level of a structure to be monitored, which can be distributed in arbitrary directions and which can vary over time. Embodiments of the present invention uniquely utilize bonding materials, both within the structure of the apparatus and to connect the apparatus to the structure to be monitored, that are capable of withstanding high pressure and high temperature composite processing and operations, such as, for example, that associated with carbon and carbon fiber composite lamination. Particularly, embodiments of the present invention can be formed by employing a process of layering and attaching ceramic piezoelectric material, electrode interconnect conducting carrying layers, or others to form two-dimensional and three-dimensional structures which include electrical conductors and connections and/or switchology to form arbitrarily complex electrode patterns and which allow the piezoelectric composite apparatus to fit in arbitrarily small spaces, i.e., as small as 1/100th or $1/100^{th}$ of the space conventionally required.

More specifically, according to an embodiment of the present invention, a piezoelectric planar composite apparatus includes a piezoelectric electric material layer, a plurality of electrodes positioned in electrical contact with the piezoelectric material layer, and a plurality of sets of electrode interconnect conductors each positioned in electrical contact with a different subset of the plurality of electrodes and positioned to form a plurality of complementary electrode patterns. Each of the plurality of complementary electrode patterns is configured to form an electric field having an electric field axis oriented along a different physical axis from that of an electric field formed by at least one other of the complementary electrode patterns. Advantageously, this allows user selection of a different electric field axis depending upon which complementary electrode pattern is selected. According to one embodiment, the sets of interconnect conductors are in the same plane and provide for establishing an N×N electrode matrix. According to another embodiment, sets of electrode interconnect conductors are distributed over a plurality of electrode interconnect conductor carrying layers each carrying a different one of the plurality of sets of electrode interconnect conductors.

Embodiments of the apparatus can provide a three-dimensional array of electrode interconnect conductors configured to either include or interface with a switching device to allow automated selection of a subset of the electrodes to thereby select the direction of the electric field to coincide with usable strain or as otherwise desired. That is, according to an embodiment of the present invention, the piezoelectric planar composite apparatus is configured so that when the apparatus (and thus the associated piezoelectric material) is operatively positioned within or on a structure to be monitored having an axis of usable strain or operatively positioned within or on a structure to which energy harvesting is to be performed, each of the plurality of complementary electrode patterns are separately selectable to allow the user to select the complementary electrode pattern providing an electric field axis most closely matching the usable axis of usable strain.

The usable axis of strain, however, can vary over the time. As such, embodiments of the apparatus can also provide for adaptive selection of the electrodes or shaping of electrode patterns as a function of time. The piezoelectric planar composite apparatus can include a mechanical switch, a microprocessor, or a combination thereof to allow user electrode pattern selection to correspondingly vary over time, or as otherwise desired by the user or as selected by the microprocessor and associated algorithms.

Embodiments of the apparatus allow for positioning of the apparatus in arbitrarily small locations on or adjacent a structure and in arbitrary orientations. Particularly, embodiments of the piezoelectric composite apparatus can allow the user to electrically switch off and on particular electrodes to form a plurality of separately distinct complementary electrode patterns so that the electric field generated by the piezoelectric material is substantially aligned with the presently existing axis of usable strain without physically changing the position of the piezoelectric apparatus. Embodiments of the apparatus alternatively can provide the ability to select from a plurality of preselected distinct complementary electrode patterns rather than individual electrodes forming the electrode patterns to provide for manipulation of the electric field orientation.

In order to connect to or be positioned or laminated within the structure to be monitored, embodiments of the apparatus can include an apparatus interconnect layer positioned to connect the apparatus with the structure to be monitored. When the apparatus is to be, for example, interlaminated within the structure to be monitored during formation thereof and the structure to be monitored (during such formation) requires very high temperatures and pressures such as that required by a carbon fiber structure or carbon epoxy, the interconnect layer can include a very high temperature resin such as an addition-type polyimide resin which includes characteristic capabilities to enable the piezoelectric planar composite apparatus to withstand a pressure of at least approximately 100 PSI at temperature of at least approximately 190° C. for approximately six hours without failure during the interlamination within the composite structure during formation thereof.

Embodiments of the present invention also include methods of forming the piezoelectric composite apparatus. According to an embodiment of a method, blocks of fired piezoelectric material, e.g., PZT, are cut into slices of thin wafers. These wafers are bonded together in a stack using a high temperature film adhesive or resin. The stack is sliced again in the perpendicular direction creating composite wafers of PZT fibers and resin. These composite wafers are then laminated directly to or between a dielectric material such as Kapton® using a liquid high temperature resin. Electrodes on the Kapton® or directly on the PZT fibers can create an electric field in the plane of the assembled, composite wafer to align the major piezoelectric poling axis with the direction of strain to be measured. According to an embodiment of the method, multiple layers of Kapton® carrying electrode interconnect conductors connecting to different combinations of electrodes can be stacked on either or both sides of the PZT fibers. Various combinations of the electrodes can be connected to a data acquisition system to measure output charge that is related to voltage and in this example, strain. Advantageously, this manufacturing and installation process can produce sensors that can be embedded or surface bonded to composite structures and that are significantly stronger, operate at higher temperatures, and facilitate higher output when compared with similar existing sensors.

According to another embodiment of the method, the piezoelectric planar composite apparatus can be formed using photographic and/or chemical processing steps and methodologies similar to that used for manufacturing semiconductor devices. For example, according to an embodiment of the method, a piezoelectric planar composite apparatus having either a simple or complex electrode design is formed in layers on either a substrate or directly on a piezoelectric material layer. Regardless, a conductive layer, e.g., a metal like nickel, which forms the electrodes, is deposited on the piezoelectric material. The nickel is then patterned with photoresist and etched with a corrosive solution. A layer of an insulator, e.g., silicon nitride, is then deposited on the nickel along the nickel pattern. The silicon nitride is then patterned to define contacts and is etched using a corrosive. A layer of metal, e.g., nickel, is then deposited on the silicon nitride. This nickel layer is then patterned with photoresist to define the electrode interconnect conductors and electrode connection pads and etched with a corrosive solution. The above steps can then be repeated for the other side of the substrate or directly on the other side of the piezoelectric material if a substrate was not used.

BRIEF DESCRIPTION OF THE DRAWINGS

So that this manner in which the features and advantages of the invention, as well as others which will become apparent, may be understood in more detail, a more particular description of the invention briefly summarized above may be had by reference to the embodiments thereof which are illustrated in the appended drawings, which form part of this specification. It is to be noted, however, that the drawings illustrate only various embodiments of the invention and are therefore not to be considered limiting of the invention's scope as it may include other effective embodiments as well.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numerals refer to like elements throughout. Prime notation, if used, indicates similar elements in alternative embodiments.

Figure 1:
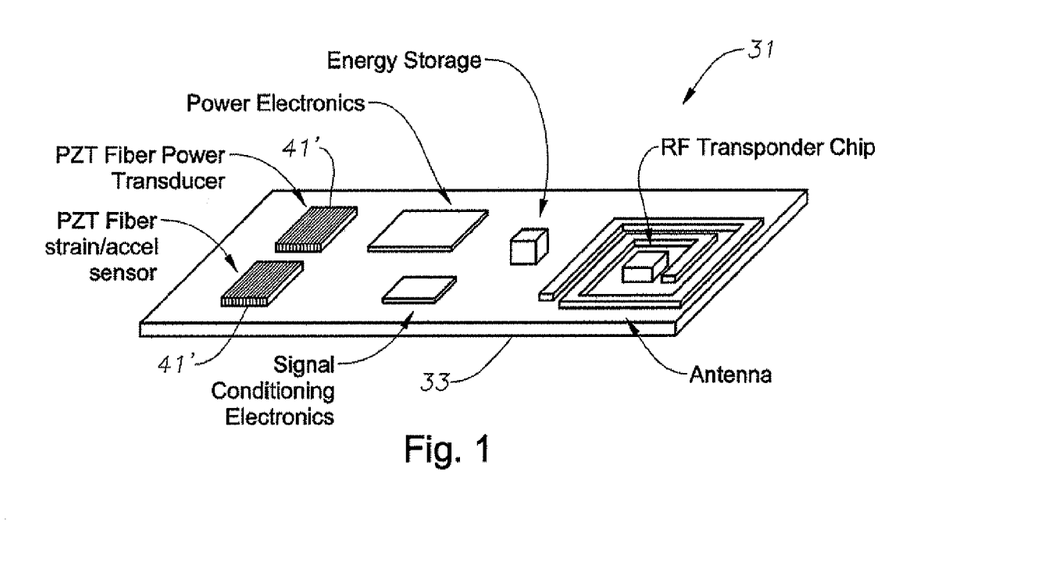
FIG. 1 is a schematic diagram of a general system architecture of a health monitoring system according to an embodiment of the present invention.
Figure 2:
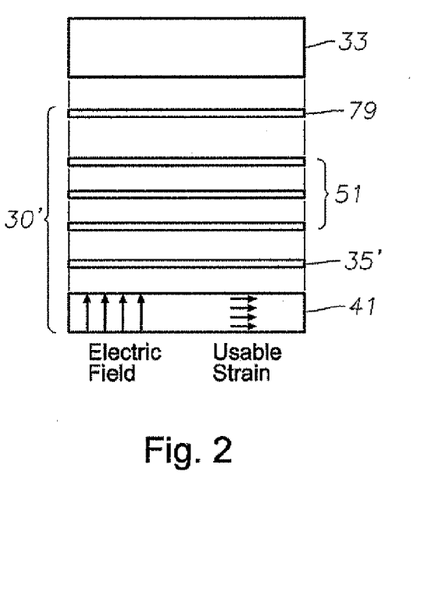
FIG. 2 is an exploded schematic diagram of a piezoelectric planar composite apparatus and structure to be monitored according to an embodiment of the present invention.
Figure 3:
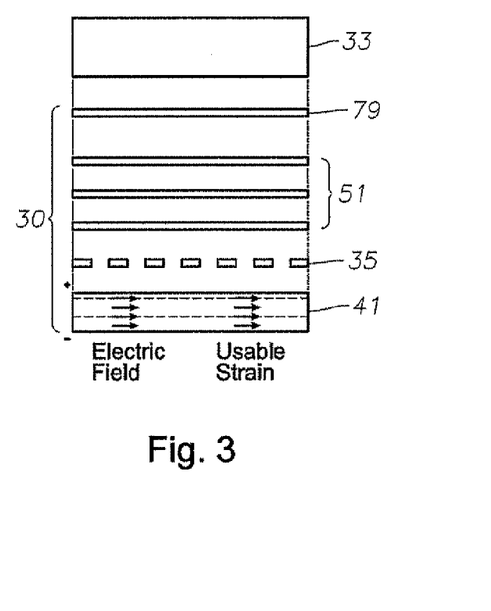
FIG. 3 is an exploded schematic diagram of a piezoelectric planar composite apparatus and structure to be monitored according to an embodiment of the present invention.
Figure 4:
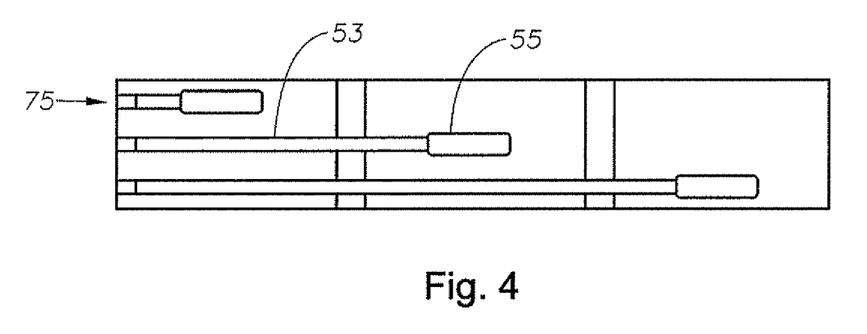
FIG. 4 is a top plan view of unbalanced electrical contacts, electrode interconnect conductors, and an electrode interconnect conductor carrying layer according to an embodiment of the present invention.
Figure 5:
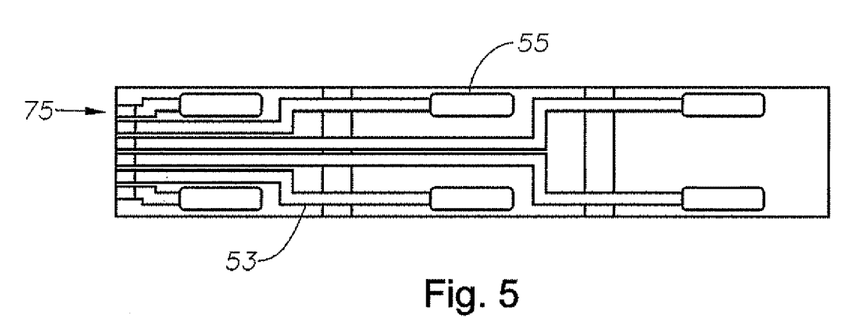
FIG. 5 is a top plan view of balanced electrical contacts, electrode interconnect conductors, and an electrode interconnect conductor carrying layer according to an embodiment of the present invention.

As perhaps best shown in FIGS. 1-3, in general, embodiments of the present invention provide a piezoelectric planar composite apparatus 30, 30', which can be integrated with other integrated systems 31, for example, health monitoring systems, such as that described in U.S. patent application Ser. No. 11/430,410 by Sealing, et al. titled "System to Monitor the Health of a Structure, Program Product, and Related Methods," filed on May 9, 2006. Embodiments of the piezoelectric planar apparatus 30, 30' can be positioned in an arbitrarily small area and in arbitrary orientations within or in contact with a structure to be monitored 33 to provide both health monitoring and power harvesting functions. To do so, various embodiments of the apparatus 30, 30' provide for adaptive selection of the electrodes 35, 35' (FIGS. 4-13C, and 23-24) connected to or otherwise in contact with a piezoelectric material 41, 41', or shaping or selection of electrode patterns to adaptively align the orientation of the electric field with the direction of usable strain or axis of strain to enhance energy transfer (see, e.g., FIG. 3). Advantageously, such feature can make the apparatus 30, 30' positionable in the arbitrarily small areas with arbitrary orientations during or in conjunction with formation, repair, or retrofitting of the structure 31. Note, according to various configurations of the structure to be monitored 33, orientation of layers forming the structure to be monitored 33 can affect the direction of usable strain. Note further, although generally equally applicable to the structure on both sides of the apparatus 30, 30', for simplicity, the following discussion and illustrations are primarily directed to only one side.

As perhaps best shown in FIG. 3, embodiments of the piezoelectric planar composite apparatus 30 can include a piezoelectric material 41 such as, for example, lead zirconate titanate (PZT), barium titanate, zirconia, aluminum nitride, gallium nitride, zinc oxide, or others known to those skilled in the art, which can be embedded, aligned, and mechanically and electrically connected to form a durable sensor and energy harvester based on piezoelectric and/or strain gage technologies. Piezoelectric material 41' can include macro fiber composites (MFC) or others as known to those skilled in the art. According to embodiments of the present invention, the piezoelectric apparatus 30 is in the form of a solid or layered piece of piezoelectric material 41 (see, e.g., FIGS. 2 and 3) or piezoelectric fibers 41' (FIGS. 1 and 15) forming a piezoelectric fiber matrix. Electrodes 35 are either directly positioned (e.g., FIGS. 2 and 3) or indirectly positioned (e.g., FIGS. 23 and 24) in electrical contact with the piezoelectric material 41, 41'.

As perhaps best shown in FIGS. 2 and 3, the apparatus 30 can include one or more electrode insulating layers defining electrode interconnect conductor carrying layers 51 stacked or otherwise layered adjacent the piezoelectric material 41, 41'. According to the illustrated embodiments, the electrode interconnect conductor carrying layers 51 include an insulating material such as a glass epoxy, a polyimide such as Kapton® manufactured by DuPont®, silicon nitride ($Si_3N_4$), or others known to those skilled in the art, depending upon various factors including temperature-pressure considerations related to the structure to be monitored 33. These layers 51 can carry electrode interconnect conductors 53 and/or electrode conductor pads 55 (see, e.g., FIGS. 4-5 and 12-13A).

The electrode interconnect conductors 53 and pads 55, as with the electrodes 35, can include an electrically conductive material such as, for example, nickel, copper, gold, tungsten, aluminum, silver, or others known to those skilled in the art. The electrode interconnect conductor carrying layers 51 can be anisotropically conductive along their thickness and non-conductive along their width and length. That is, the layers 51 can include multiple conductive multilevel pathways or interconnects "vias" (not shown) as known to those skilled in the art that are in contact with the electrode interconnect conductors 53 and/or pads 55, which can provide an electrical pathway between the electrode interconnect conductors 53 and/or pads 55 and the electrodes 35, or between the electrodes 35 and the piezoelectric material 41, 41', if so configured.

In the embodiments having electrodes 35 directly in contact with the piezoelectric material 41, 41', where multiple layers 51 are present on a single side, the innermost layers 51 can include additional conductive pathways or vias (not shown) which allow the electrode interconnect conductors 53 and/or pads 55 to establish an electrical pathway to the electrodes 35 and ultimately to the piezoelectric material 41, 41' from the outer layers 51.

In the embodiments having electrodes 35 connected indirectly, the electrode interconnect conductor carrying layers 51 also carry the electrodes 35. In such embodiments, normally the electrodes 35, rather than the electrode interconnect conductors 53 and/or pads 55, are positioned in contact with the conductive pathways or vias to establish an electrical connection to the piezoelectric material. Where multiple layers 51 are present on a single side, as in the previously described configurations, the innermost layers 51 can include additional conductive pathways or vias (not shown) which allow the electrodes 35 to establish in electrical pathway to the piezoelectric material 41, 41' from the outer layers 51.

Figure 6:
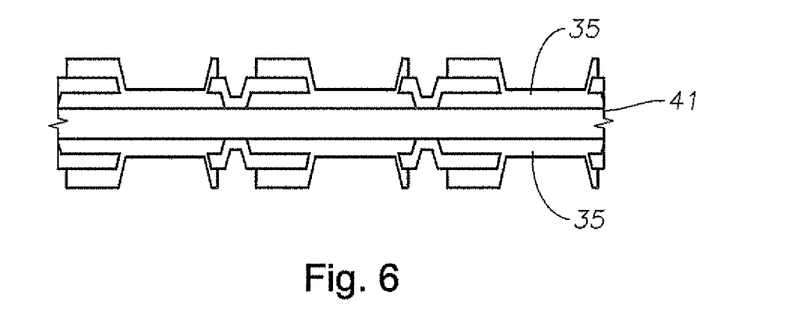
FIG. 6 is a sectional view of a piezoelectric planar composite apparatus illustrating a mono morph configuration according to an embodiment of the present invention.
Figure 7:
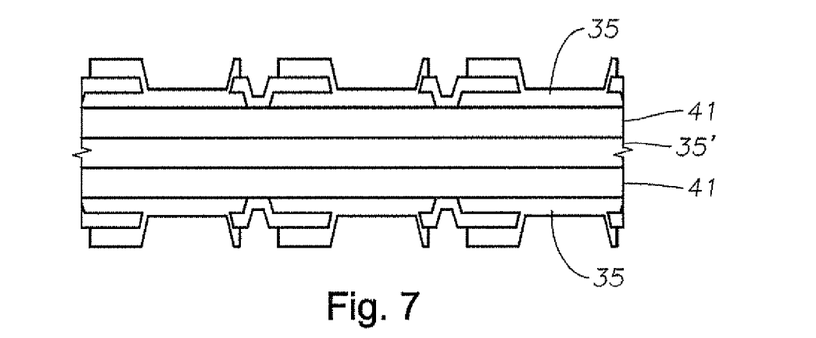
FIG. 7 is a sectional view of a piezoelectric planar composite apparatus illustrating a bimorph configuration with a common center electrode according to an embodiment of the present invention.
Figure 8:
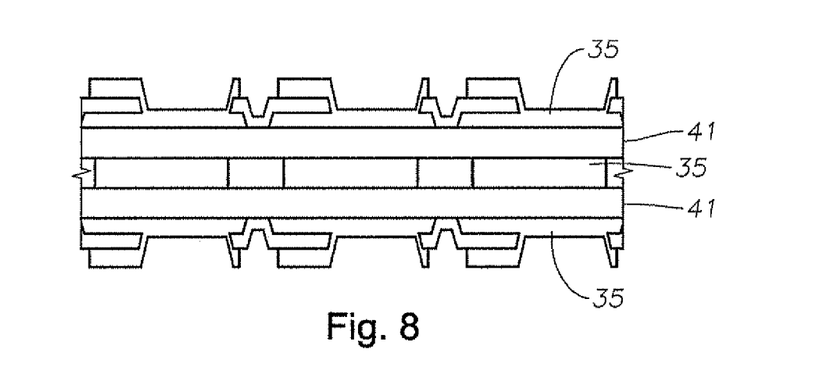
FIG. 8 is a sectional view of a piezoelectric planar composite apparatus illustrating a bimorph configuration with a distinct fixed routed central electrode according to an embodiment of the present invention.
Figure 9:
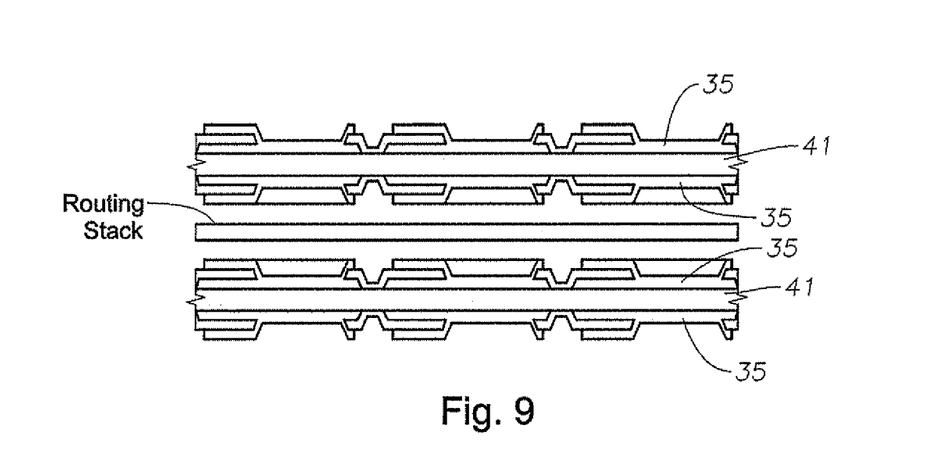
FIG. 9 is a sectional view of a piezoelectric planar composite apparatus illustrating a bimorph configuration with a distinct routable central electrode according to an embodiment of the present invention.
Figure 23:
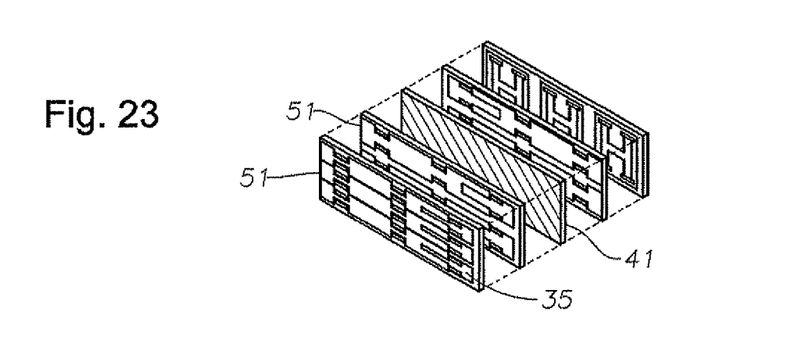
FIG. 23 illustrates an exploded perspective view of a piezoelectric planar composite apparatus having multiple electrode interconnect conductor carrying layers on either side of a piezoelectric material structure carrying electrode interconnect conductors forming multiple complementary electrode patterns according to an embodiment of the present invention.
Figure 24:
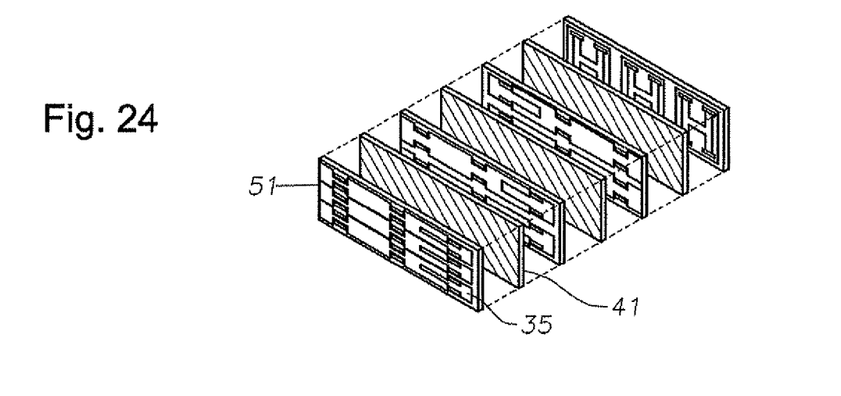
FIG. 24 illustrates an exploded perspective view of a piezoelectric planar composite apparatus having a single electrode interconnect conductor carrying layer on either side of a piezoelectric material structure carrying electrode interconnect conductors forming multiple complementary electrode patterns according to an embodiment of the present invention.

The above described structures can be repeated on the other side of the piezoelectric material 41, 41', as perhaps best shown in FIGS. 6-9 and 23 and 24. FIG. 6 illustrates a mono morph configuration of a functional portion of the apparatus 30. FIG. 7 illustrates a bimorph configuration of a functional portion of the apparatus 30 with a common center electrode 35'. FIG. 8 illustrates a bimorph configuration of a functional portion of the apparatus 30 with a distinct fixed routed central electrode 35. FIG. 9 illustrates a bimorph configuration of a functional portion of the apparatus 30 with a distinct routable central electrode 35'. FIG. 23 illustrates a portion of apparatus 30 having multiple electrode interconnect conductor carrying layers 51 positioned on either side of the piezoelectric material 41 and carrying electrodes 35, pads 55, and electrode interconnect conductors 53 to form multiple complementary electrode patterns. FIG. 24 illustrates a portion of the apparatus 30 having a single electrode interconnect conductor carrying layer 51 on either side of the piezoelectric material 41, and carrying electrodes 35, pads 55, and electrode interconnect conductors 53 to forming multiple complementary electrode patterns across the piezoelectric material 41. Providing electrodes 35, interconnect conductors 53, and/or electrode interconnect conductor carrying layers 51 including electrode interconnect conductors 53 on opposite sides of the piezoelectric material 41, 41', can result in different effects such as, for example, doubling the voltage or the power that can be received.

As perhaps best shown in FIGS. 2-13C, and 22-24, the combination of electrode patterns and/or the combination the multiple electrode interconnect conductor carrying layers 51 can form two or three-dimensional array of electrode interconnect conductors 53, which allow for the selection of various combinations of the electrodes 35. The various combinations of electrodes 35: intra layer on one or more layers 51 (see, e.g., FIGS. 10-13A); interlayer on one side of the piezoelectric material 41 (see, e.g., FIG. 23); interlayer over more than one side of the piezoelectric material 41 and/or more than one layer of piezoelectric material 41 (see, e.g., FIGS. 6-9 and 22-24); or a combination thereof, can provide for selection of multiple complementary electrode patterns selectable to form an electric field along an axis selected by the user. Beneficially, such selection allows the user to orient the electric field axis along different desired physical axes which, according to the exemplary embodiment, would most nearly coincide with the usable axis of strain, thus, potentially maximizing energy transfer between the structure 33 and the apparatus 30, 30'.

Figure 10:
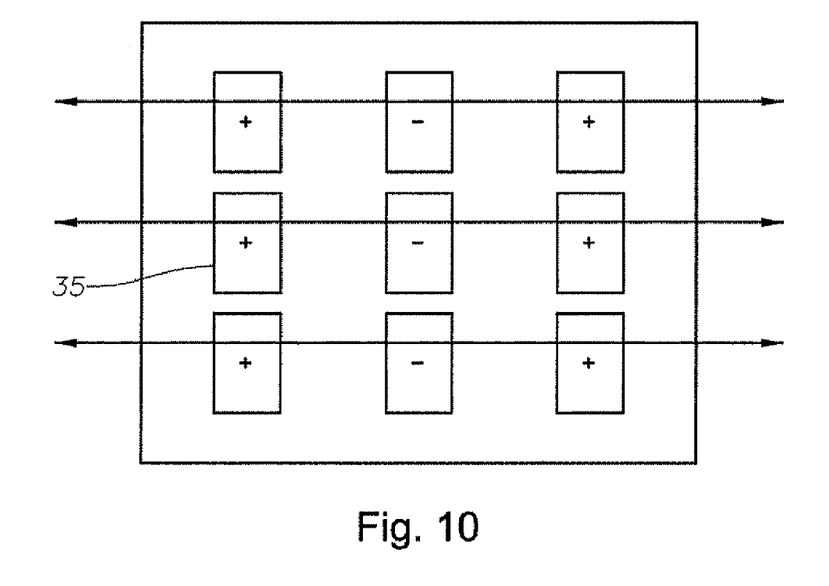
FIG. 10 is a schematic diagram of an N×N electrode matrix producing an electric field along a first electric field axis according to an embodiment of the present invention.
Figure 11:
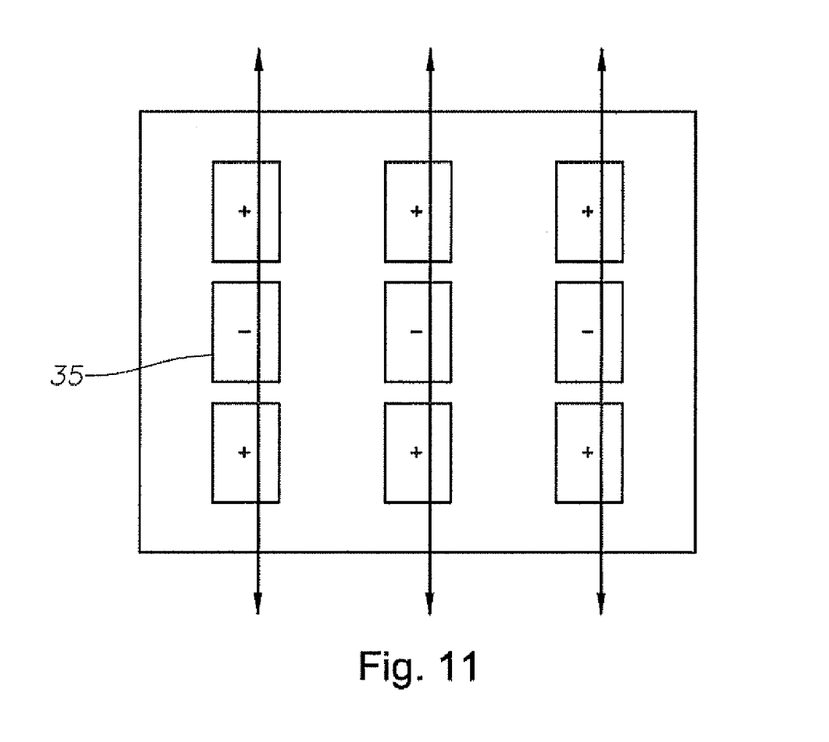
FIG. 11 is a schematic diagram of the N×N electrode matrix illustrated in FIG. 6 producing an electric field along a second electric field axis according to an embodiment of the present invention.
Figure 12:
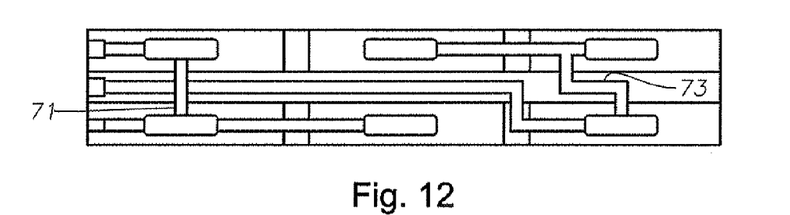
FIG. 12 is a top plan view of electrical contacts, electrode interconnect conductors, a through routing stack, and an electrode interconnect conductor carrying layer according to an embodiment of the present invention.
Figure 13A:
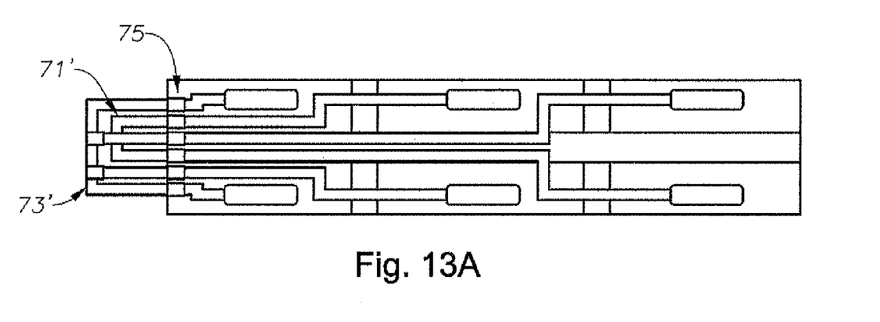
FIG. 13A is a top plan view of electrical contacts, electrode interconnect conductors, and an electrode interconnect conductor carrying layer, and a customized interconnect according to an embodiment of the present invention.
Figure 13B:
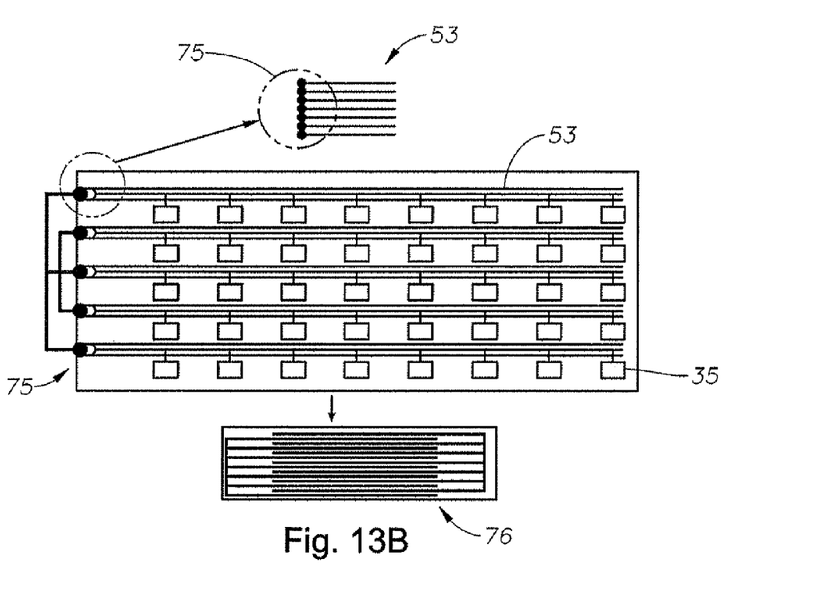
FIG. 13B is a schematic view of an electrode configuration for a default electrode selection according to an embodiment of the present invention.
Figure 13C:
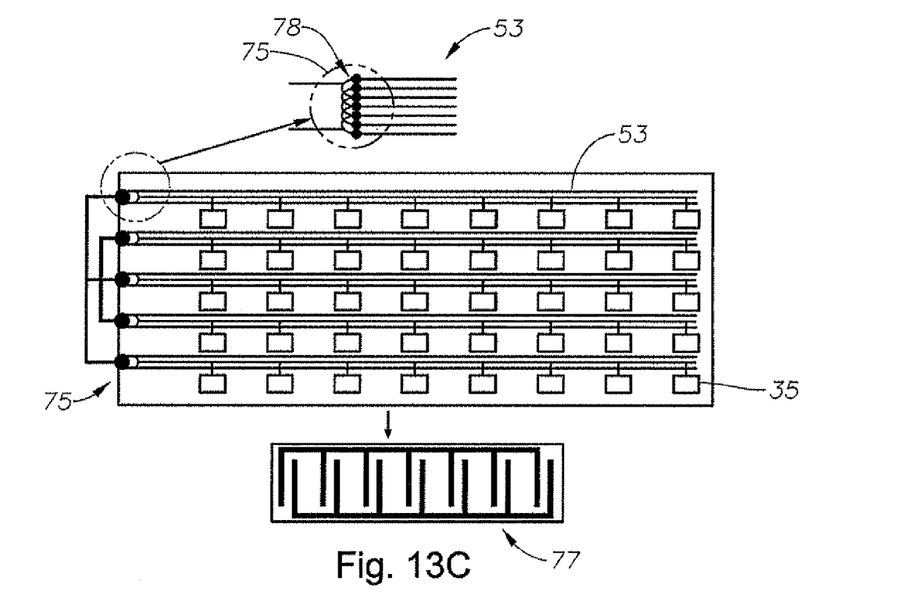
FIG. 13C is a schematic view of an electrode configuration of FIG. 13B after electrode selection according to an embodiment of the present invention.

For embodiments having electrodes 35 directly in contact with the piezoelectric material 41, 41'; for embodiments having multiple sets of electrodes 35 also in the same plane, but in indirect contact with the piezoelectric material 41, 41'; and for embodiments having multiple sets of electrodes 35 in different planes; different sets of electrode interconnect conductors 53 can access the different sets of electrodes 35 to form the complex and/or complementary two-dimensional or three-dimensional electrode patterns. For example, according to one configuration, different electrode interconnect conductors 53 within the same layer (intra layer) can be utilized to select one or more sets of the electrodes 35 (see, e.g., FIGS. 10-13C). FIGS. 10 and 11 illustrate for an N×N matrix of electrodes 35 how selectively changing electrodes 35 from positive to negative or vice versa can change the orientation of the electric field. FIG. 12 illustrates electrode pads 55 configured through a "through routing stack" 71 and through a "customized interconnect" 73 positioned with the electrode interconnect conductors 53. FIG. 13A illustrates electrode pads 55 connected through an external "through routing stack" 71' and a customized interconnect 73' connected to connectors 75. FIGS. 13B-C illustrate exemplary combinations of equivalent electrode pad/electrode configurations 76, 77, obtainable through selection/interconnect customization of combinations of electrode interconnect conductors 53 through connectors 75. Specifically, FIG. 13C illustrates formation of a different electric configuration 77 and that of configuration 76 (FIG. 13B) through the use of jumpers 78.

In another configuration, different sets of electrode interconnect conductors 53 across different layers 51 can be utilized to select one or more sets of the electrodes 35 (see, e.g., FIGS. 4-5 and 12-13C), thus allowing three-dimensional orientation of the electric field. In still a further configuration, one or more of the above can be used in conjunction with one or more layers 51 including electrode interconnect conductors 53 on the opposite side of the piezoelectric material 41, 41' (see, e.g., FIGS. 6-9, and 23-24). In yet another configuration, individual layers 51 can provide for access of a predetermined set of electrodes 35 such as those shown in FIG. 22. That is, a user can select a single layer 51 or a combination of layers 51 to access predetermined sets of electrodes 35. Note, the above illustration and discussion equally applies to both embodiments where the electrodes 35 are positioned in a single plane on either side of the piezoelectric material 41, 41', and where the electrodes 35 are positioned on separate interconnect conductor carrying layers 51 along with the electrode interconnect conductors 53.

Embodiments of the apparatus 30 can include a switch 61 (see, e.g., FIG. 22) to allow a user a one-time electrode pattern selection and/or to allow user electrode pattern selection to vary over time, such as, for example, where the axis of usable strain also varies over time, e.g., according to the configurations immediately described above. The switch 61 can be mechanical or electrical, etc., automated or manual, as known to those skilled in the art. Instead of or in addition to using switch 61, selection of conductors 53 can be as simple as making conductive connections, for example, directly to connectors 75 (see, e.g. FIGS. 4 and 5) to allow a "set and forget" selection methodology and/or to allow for microprocessor selection according to the configurations immediately described above. These conditions can be either permanent, temporary, and/or time-varying.

As perhaps best shown in FIGS. 2 and 3, the piezoelectric electric composite apparatus 30, 30', can comprise an interface (interconnect) material 79 including a suitable high-temperature resin to connect the apparatus 30, 30' to the structure to be monitored 33 or to an intermediate material associated with the structure to be monitored 33, e.g., a graphite epoxy composite. Such interface material 79 can include, for example, glass epoxy, graphite epoxy, or others known to those skilled in the art such as those available under various trade names, e.g., 3M, 1469, Newport NB 101, Newport NB 301, Cytec 977, Hexcel Redux 319, ULTEM, Masterbond EC-30, Epotec 375, Loctite E-120 HP, SPIE, etc. Such material 79 can allow the finished apparatus 30, 30', to withstand temperatures of up to approximately 150° C.-160° C. and pressures of up to 90 PSI for six hours generally required for the construction of many conventional structures to be monitored 33. Note that when embedding the sensor at 150° C., the sensor is normally cooled in a stress condition as the epoxy cools, and this strain, should be accounted for in the calibration.

Where the piezoelectric electric composite apparatus 30, 30', is to be embedded within or otherwise subjected to extreme manufacturing temperatures and/or pressures associated with the manufacture of, for example, a carbon fiber structure to be monitored 33, the interface material 79 should include a suitable high-temperature resin such as, for example, Bismaleimide (BMI), or other addition-type polyimide or maleimide-based polyimide resin to interface the apparatus 30, 30' to the structure to be monitored 33 or to an interface material associated with the structure to be monitored 33, e.g., a graphite epoxy composite. Such high-temperature resins can allow the finished apparatus 30, 30', to withstand temperatures of upwards of 190° C. or more and pressures of upwards of 100 PSI or more for six hours generally required for the construction of, for example, carbon fiber composite structures.

Figure 14:
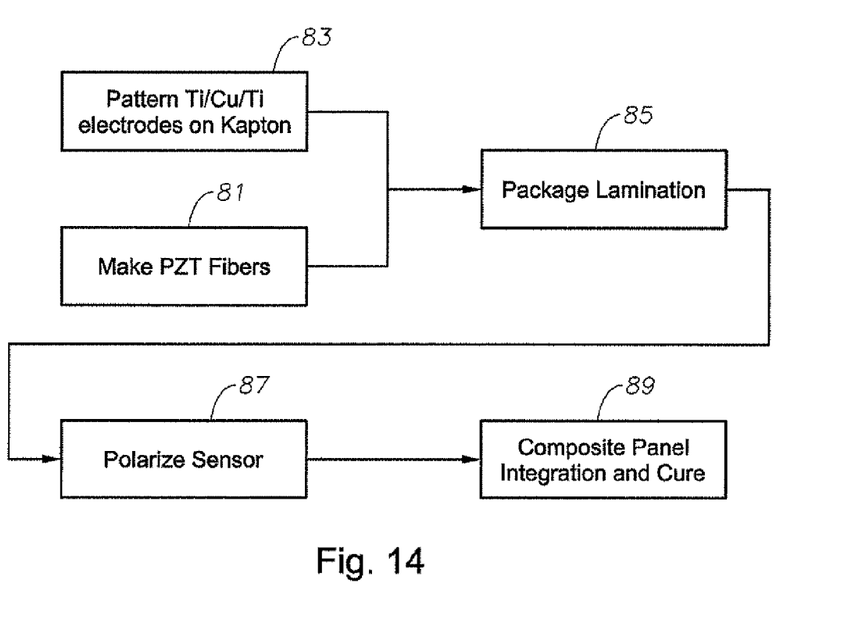
FIG. 14 is a schematic flow diagram of a method of forming a piezoelectric planar composite apparatus according to an embodiment of the present invention.
Figure 15:
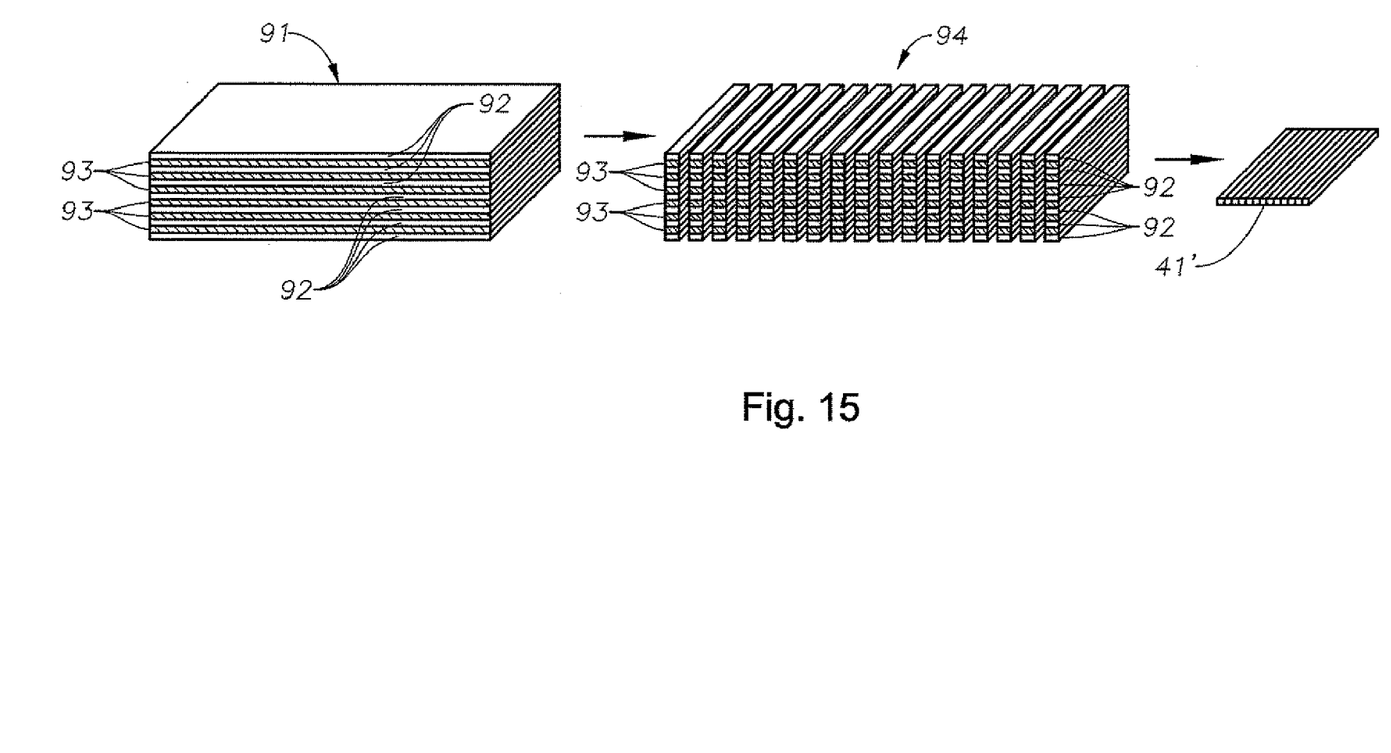
FIG. 15 is a schematic flow diagram illustrating formation of a piezoelectric fiber matrix according to an embodiment of the present invention.

As shown in FIGS. 16-21, embodiments of the present invention include methods of forming the piezoelectric composite apparatus 30, 30'. The methods can include use of either a single or layered piece of piezoelectric material, e.g., PZT, etc., such as the material 41 shown in FIGS. 2 and 3, or as indicated in block 81 of FIG. 14, piezoelectric material in the form of a multi-strand wafer 41' (e.g., piezoelectric fiber matrix) such as that manufactured as shown in FIG. 15, described in more detail below. As indicated in block 83, electrodes 35 can then be patterned either directly on the piezoelectric material 41, 41', as shown in FIGS. 2 and 3, or on one or more pieces of insulating material, e.g., Kapton®, defining an electrode interconnect conductor carrying layer 51 having multiple conductive channels or vias (not shown) extending therethrough. As indicated in block 85, and as perhaps best shown in FIGS. 2 to 3, the layers of material forming the piezoelectric composite apparatus 30, 30', are assembled using, for example, a package lamination technique, incorporating an interface material 79, e.g., adhesive or resin, to thereby form or assemble portions of the apparatus 30, 30'.

Use of the package lamination technique identified above can be desirable as it can help solve some of the problems including those associated with piezoelectric material/electrode alignment, release imprint on the Kapton®, collapse of wafer during cure, wafer edge quality, wafer swimming, fiber breakage, adhesive/solvent splotches, wrinkling, bond line thickness, metallization indents, voids, unintended release sheets in laminate, and wafer stack debonding. As indicated in block 87, the piezoelectric composite apparatus 30, 30', is then optionally polarized to provide a default polarization direction. In a preferred methodology, a voltage is applied either through the electrode interconnect conductors 53 or directly to the electrodes 35 to enhance the polarization process. As indicated in block 89, the piezoelectric composite apparatus 30, 30', is then integrated with the structure to be monitored 33. Integration can be, for example, through inter lamination or integration with a surface of the structure. As indicated above, where the structure to be monitored 33 requires the apparatus 30, 30', to be subjected to very high curing temperatures and/or pressures, such as with carbon fiber composite structures, the interface material can include a resin such as, for example, BMI.

According to an embodiment of the method as shown in FIG. 15, blocks of fired piezoelectric material 41, e.g., PZT, are cut into slices of thin wafers to form a stack 91. These wafers 92 are bonded together in the stack 91, for example, using a high temperature film adhesive or resin 93. The stack 91 is sliced again in the perpendicular direction as shown at 94, creating composite wafers of piezoelectric material fibers and resin defining the planar piezoelectric composite 41'. As described above, these composite wafers or materials 41' are then laminated directly to electrodes 35 or in contact with or between electrode interconnect conductor carrying and/or electroded dielectric material 51 (e.g. dielectric material patterned with conductive material) such as Kapton®, for example, using a liquid high temperature resin or other known methodology, or using material such as, for example, BMI, where the post-formation apparatus 30' is to be subjected to very high temperatures and/or pressures such as those associated with some structures to be monitored 33 (e.g., carbon fiber composites, etc.).

Regardless of the configuration of the piezoelectric material 41, 41', electrodes 35 positioned on the Kapton® or positioned directly on the piezoelectric material 41, 41', can create an electric field in the plane of the composite wafer or material 41, 41' to align the major piezoelectric poling axis with the direction of strain (see FIG. 3) or other health indication to be measured and/or used for energy harvesting.

According to an embodiment of the method, multiple layers of material 51, e.g., Kapton®, carrying the electrodes interconnect conductors 53 connecting to different combination of electrodes 35, can be stacked or layered on either or both sides of the piezoelectric material 41'. Various combinations of the electrodes 35 can be connected to or form part of the health monitoring/data acquisition system 31 to, for example, measure output charge that is related to voltage which is related to health of the structure, strain in this example, and/or to harvest energy from the structure to be monitored 33. This manufacturing and installation process can produce sensors that can be embedded within or bonded to composite structures to be monitored 33 that are significantly stronger, operate at higher temperatures, and facilitate higher output compared with similar existing sensors.

According to another embodiment of the method, the piezoelectric planar composite apparatus 30, 30', can be formed using photographic and/or chemical processing steps and methodologies similar to that used for manufacturing semiconductor devices. For example, according to an embodiment of a method, a piezoelectric planar composite apparatus 30, 30', having either a simple or complex electrode design is formed in layers on either a substrate 101 (see, e.g., FIGS. 16-21) or directly on piezoelectric material 41, 41' (see, e.g., FIGS. 6-9). FIGS. 16-21 illustrate an exemplary application of this layering methodology beginning with substrate 101.

Figure 16:
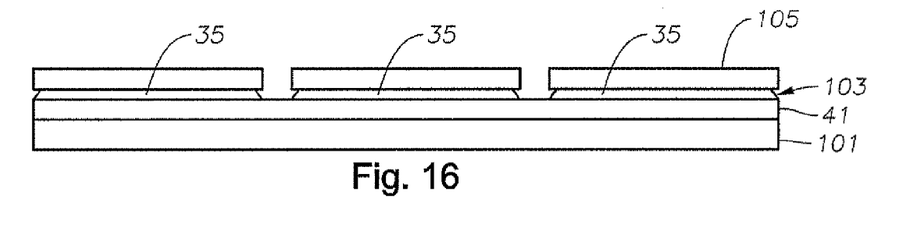
FIGS. 16-21 is a sectional view of a single layer piezoelectric planar composite apparatus illustrating layer-by-layer formation thereof according to an embodiment of the present invention.

As perhaps best shown in FIG. 16, the piezoelectric material 41 is deposited on the substrate 101, and a metal layer 103, e.g., nickel, etc., which forms the electrodes 35, is deposited on the piezoelectric material 41. The nickel is then patterned using photoresist 105, and etched with a corrosive etching solution, e.g., ferric chloride, a hydrogen chloride, nitric acid, octafluorocyclopentene, reactive ion etching, or dry etching methods is known to those skilled in the art.

Figure 17:
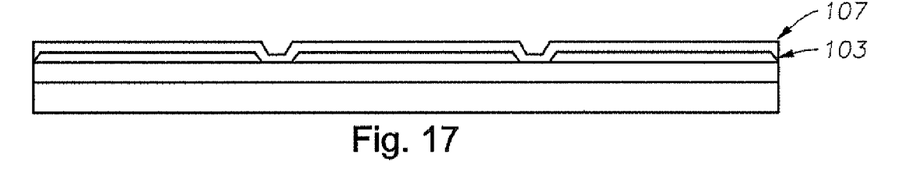

As shown in FIG. 17, a layer of an insulator 107, e.g., silicon nitride, is then deposited on the nickel along the nickel pattern. This can be accomplished using chemical vapor deposition (CVD) method, or one of its variants, such as plasma-enhanced chemical vapor deposition (PECVD).

Figure 18:
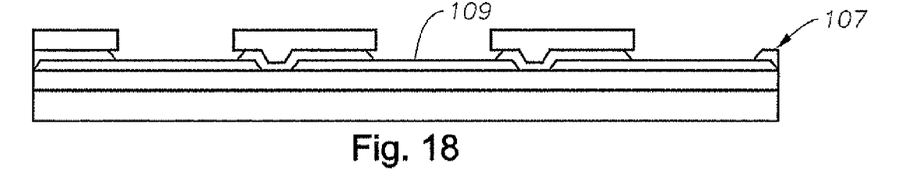
Figure 19:
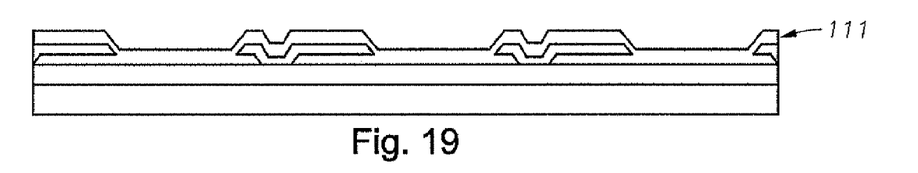

As shown in FIG. 18, the silicon nitride is then patterned to define electrode contacts 109 and is etched using a corrosive such as hot phosphoric acid, and as shown in FIG. 19, a layer of metal 111, e.g., nickel, is then deposited on the silicon nitride. A sputtering process can be used to deposit a thin-film adhesion layer of metal, e.g., titanium or nickel, followed by an electroplating step, to deposit a thicker layer of the metal.

Figure 20:
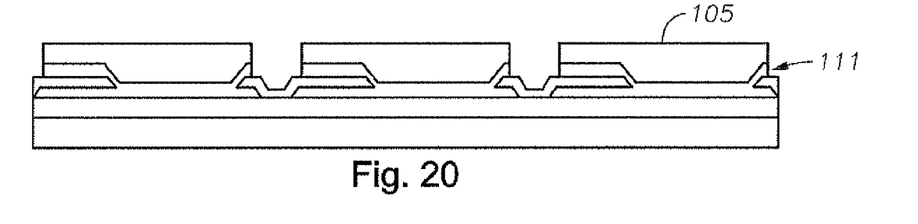
Figure 21:
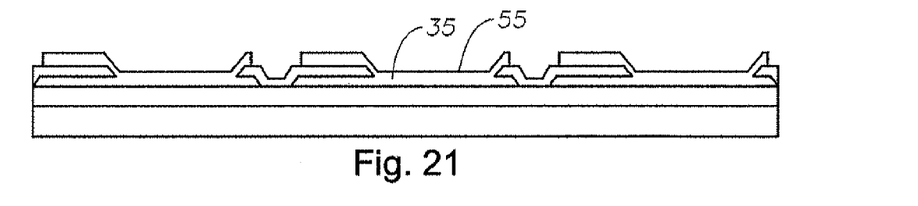
Figure 22:
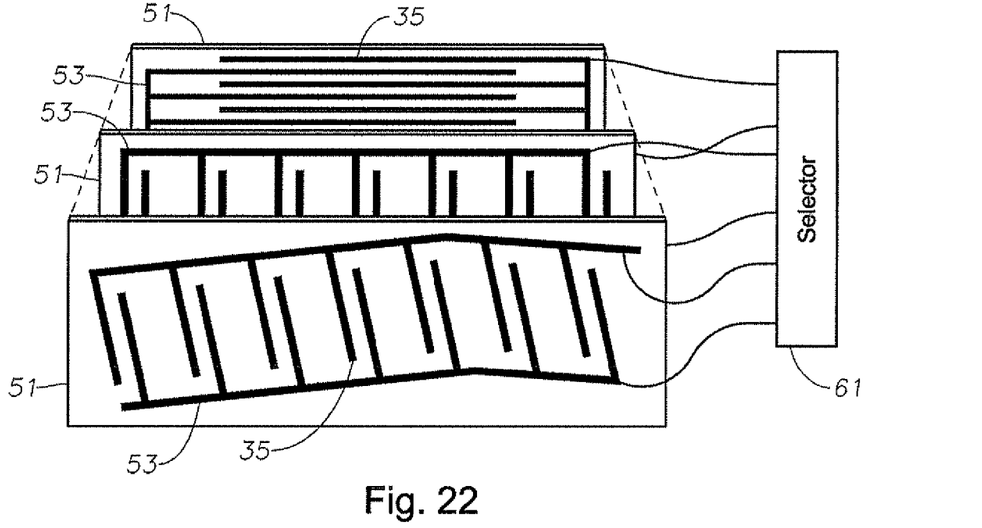
FIG. 22 illustrates a partially exploded perspective view of a piezoelectric planar composite apparatus having multiple electrode interconnect conductor carrying layers carrying electrode interconnect conductors forming multiple complementary electrode patterns selectable by a switch according to an embodiment of the present invention.

As shown in FIG. 20, the layer 111 can be patterned with photoresist 105 to define the electrode interconnect conductors 53 and electrode connection pads 55 and etched with a corrosive solution, e.g., ferric chloride or a hydrogen chloride or nitric acid. If titanium is used, the layer 111 can be etched using a wet etchant typically used in the manufacture of thin film transistors. The result is the exemplary "single layer" piezoelectric composite apparatus 30 illustrated in FIG. 15.

As perhaps best shown in FIGS. 2 and 3, multiple layers of a combination of metal forming the electrode interconnect conductors 53 and/or electrode connection pads 55 and of a combination of anisotropically conductive insulator layers 51, e.g., Kapton® having multiple vias (not shown), defining electrode interconnect conductor carrying layers 51, can then be applied and etched over the metal layer 111 to provide a three-dimensional array of the electrode interconnect conductors 53 and pads 55 (in the direct electrode configuration) or electrodes 35 (in the indirect electrode configuration). Such configuration provides the necessary routing to an external interface either on a sectional basis (e.g. selection or deselection of various interconnect conductors 53 within each single layer) or on a layer-by layer basis (e.g., selection or deselection of whole layers 51 of interconnect conductors 53). Note, for simplicity FIGS. 2 and 3 illustrate the electrode interconnect conductor carrying layers 51 without the electrode interconnect conductors 53 or pads 55. The above steps can then or simultaneously also be replaced for the other side of the substrate or directly on the other side of the piezoelectric material if a substrate was not used.

According to a preferred embodiment of the present invention, the completed piezoelectric composite apparatus 30, 30', is then poled by applying a voltage through the electrode interconnect conductors 53 to the electrodes 35 using techniques known to those skilled in the art, to provide a default configuration. If a sufficient voltage source is available, the completed apparatus 30, 30', can be selectively poled after installation or can have its poling updated or reset, for example, to substantially or at least partially align the e-field parallel to, e.g., usable strain (i.e., aligning the major piezoelectric polling axis with strain to be measured), to enhance energy transfer.

Upon being physically deformed, the piezoelectric material 41, 41', generates an electrical potential between the electrodes 35 which is conducted through the electrode interconnect conductors 53 to a processor for signal measurement and/or to a storage device to be harvested.

The invention has several advantages. Embodiments of the apparatus allow the user to electrically switch off and on particular electrodes to form a plurality of separately distinct complementary electrode patterns so that the electric field generated by the piezoelectric material is substantially aligned with the presently existing axis of usable strains, without physically changing the position of the piezoelectric apparatus. Embodiments of the apparatus also provide the ability to select from a plurality of preselected distinct complementary electrode patterns to provide for manipulation of the electric field orientation. Embodiments of the apparatus provide a three-dimensional array of electrode interconnect conductors configured to either include or interface with a switching device to allow automated selection of a subset of the electrodes to thereby select the direction of the electric field to coincide with usable strain. Embodiments of the apparatus provide for adaptive selection of the electrodes or shaping of electrode patterns as a function of time.

Advantageously, embodiments of the present invention enable the use of piezoelectric material including, for example, PZT or PZT fibers in many forms, to be connected using a high-temperature interconnect process which allows piezoelectric-based sensors or actuators (e.g., apparatus 30, 30') to withstand upwards of approximately 100 PSI and 190° C. for six hours without failure to thereby allow for embedding during a carbon fiber lamination process. Advantageously, such sensors fit interlaminate with minimal disturbing to the carbon laminate structure, and enable data strain measurements to be extracted from the carbon composite structure. These sensors may be embedded within the composite structure, or added or retrofitted to a complete structure, thus enabling old technology of un-monitored composite in use to be instrumented in a unique way. Various vehicles including aircraft, e.g., U2, SR71 Blackbird, the F22, and the like may be monitored starting at an in-use easy to retrofit configuration. Ships, planes, missiles, UAVs, munitions, man bearing bullet proof vests, tires, runways, bridges, solar panels, deep drilling well bit technology, satellites, spacecraft, and more can also be readily instrumented with these structures. According to various embodiments, the sensors are strain sensitive, and thus, can also be used for energy harvesting of electrical power, as well.

Advantageously, the piezoelectric planar apparatus 30, 30', can be part of a broader health monitoring system such as that described in, for example, U.S. patent application Ser. No. 11/287,009 by Berkean et al., titled "System to Monitor the Health of Structure, Sensor Nodes, Program Product, and Related Methods" filed Nov. 23, 2005, and U.S. patent application Ser. No. 11/398,840 by Berkean et al., titled "Broad Band Energy Harvesting System, and Related Methods" filed Apr. 6, 2006, both incorporated herein by reference in their entirety, which can include a plurality of health monitoring sensor nodes each connected to or embedded within the body of the structure to monitor data related to parameters of a portion of the body of the structure, which can be supplied power primarily by the broadband energy harvesting apparatus.

In the drawings and specification, there have been disclosed a typical preferred embodiment of the invention, and although specific terms are employed, the terms are used in a descriptive sense only and not for purposes of limitations. The invention has been described in considerable detail with specific reference to these illustrated embodiments. It will be apparent, however, that various modifications and changes can be made within the spirit and scope of the invention as described in the foregoing specification. For example, although the piezoelectric material was described almost exclusively with respect to forming a piezoelectric composite, the teachings of the present invention are equally applicable to the formation and utilization of pyroelectric composites.

The invention claimed is:

1. A piezoelectric planar composite apparatus comprising:
    a piezoelectric material layer;
    a plurality of electrodes positioned in electrical contact with the piezoelectric material layer;
    a plurality of sets of electrode interconnect conductors each positioned in electrical contact with a different subset of the plurality of electrodes and positioned to form a plurality of complementary electrode patterns, each of the plurality of complementary electrode patterns positioned to form an electric field having an electric field axis oriented along a different physical axis from that of an electric field formed by at least one other of the complementary electrode patterns; and
    a first electrode interconnect conductor carrying layer and a second electrode interconnect conductor carrying layer each carrying a different one of the plurality of sets of electrode interconnect conductors, the first electrode interconnect conductor carrying layer positioned between the piezoelectric material layer and the second electrode interconnect conductor carrying layer.

2. The apparatus as defined in claim 1, further comprising:
    a third electrode interconnect conductor carrying layer; and
    wherein the first electrode interconnect conductor carrying layer, the second electrode interconnect conductor carrying layer, and the third electrode interconnect conductor carrying layer each carrying a different one of the plurality of sets of electrode interconnect conductors, the second electrode interconnect conductor carrying layer positioned between the first electrode interconnect conductor carrying layer and the third electrode interconnect conductor carrying layer.

3. The apparatus as defined in claim 1, wherein the piezoelectric material layer includes a first and second side, the second side opposite the first side, and wherein the apparatus further comprises:
    a third electrode interconnect conductor carrying layer; and
    wherein the first electrode interconnect conductor carrying layer, the second electrode interconnect conductor carrying layer, and the third electrode interconnect conductor carrying layer each carrying a different one of the plurality of sets of electrode interconnect conductors, the third electrode interconnect conductor carrying layer positioned adjacent the first side of the piezoelectric material layer, the first and the second electrode interconnect conductor carrying layers positioned adjacent the second side of the piezoelectric material layer, and the first electrode interconnect conductor carrying layer positioned between the second side of the piezoelectric material layer and the second electrode interconnect conductor carrying layer.

4. The apparatus as defined in claim 1,
    wherein the plurality of electrodes are positioned in the same plane to define a plurality of in-plane electrodes;
    wherein the plurality of in-plane electrodes include a first set of in-plane electrodes and a second set of in-plane electrodes, the first set of in-plane electrodes positioned spaced apart from the second set of in-plane electrodes;
    wherein the plurality of sets of electrode interconnected conductors include a first set of electrode interconnect conductors electrically connected to the first set of in-plane electrodes carried on the first electrode interconnect conductor carrying layer and a second set of electrode interconnect conductors electrically connected to the second set of in-plane electrodes carried on the first electrode interconnect conductor carrying layer;
    wherein the first set of in-plane electrodes and the first set of electrode interconnect conductors form a first one of the plurality of complementary electrode patterns; and
    wherein the second set of in-plane electrodes and the second set of electrode interconnect conductors form a second of the plurality of complementary electrode patterns.

5. The apparatus as defined in claim 1,
    wherein the piezoelectric material layer when operatively positioned includes an axis of usable strain; and
    wherein the apparatus is configured so that when operably positioned each of the plurality of complementary electrode patterns are separately selectable by a user to allow the user to select the electrode pattern providing an electric field axis most closely matching the axis of usable strain.

6. The apparatus as defined in claim 5, wherein the axis of usable strain varies over time, and wherein the apparatus further comprises a switch positioned to allow user electrode pattern selection to correspondingly be varied over time.

7. The apparatus as defined in claim 1, wherein the apparatus is configured so that when operably positioned each of the plurality of complementary electrode patterns are separately selectable by a user to allow the user to align a major piezoelectric polling axis of the apparatus with a separate selected direction of strain.

8. A piezoelectric planar composite apparatus comprising:
    a piezoelectric material layer;
    a plurality of electrodes positioned in electrical contact with the piezoelectric material layer;

a plurality of sets of electrode interconnect conductors each positioned in electrical contact with a different subset of the plurality of electrodes and positioned to form a plurality of complementary electrode patterns, each of the plurality of complementary electrode patterns positioned to form an electric field having an electric field axis oriented along a different physical axis from that of an electric field formed by at least one other of the complementary electrode patterns; and an apparatus interconnected layer positioned to connect the apparatus with a carbon fiber structure or carbon epoxy, the interconnect layer comprising an addition-type polyimide resin to enable the piezoelectric planar composite apparatus to withstand a temperature of at least approximately 190° C. for approximately six hours without failure during interlamination within a composite structure during formation thereof.

9. A piezoelectric planar composite apparatus comprising:
a plurality of piezoelectric materials layers;
a plurality of electrodes each positioned in electrical contact with at least one of the plurality of piezoelectric material layers;
a plurality of sets of electrode interconnect conductors each positioned in electrical contact with a different subset of the plurality of electrodes and positioned to form a plurality of complementary electrode patterns, each of the plurality of complementary electrode patterns positioned to form an electric field having an electric field axis oriented along a different physical axis from that of an electric field formed by at least one other of the complementary electrode patterns; and
a plurality of electrode interconnect conductor carrying layers, the plurality of electrode interconnect conductor carrying layers and the plurality of piezoelectric material layers together forming a planar stack of a plurality of pairs of alternating electrode interconnect conductor carrying layers and piezoelectric material layers defining a sandwich forming a plurality of interlinked electrode patterns selectable to align a user selected one of the electric field axes with a separate selected direction of strain.

10. A piezoelectric planar composite apparatus comprising:
a piezoelectric composite material layer including a plurality of piezoelectric fibers and a plurality of strips of an interconnect material separately positioned to bond each one of the plurality of piezoelectric fibers to at least one of the other of the plurality of piezoelectric fibers to define a piezoelectric fiber matrix, the interconnect material including an addition-type polyimide resin to enable the piezoelectric planar composite apparatus to withstand a pressure of at least approximately 90 to 100 PSI at a temperature of at least approximately 190° C. for approximately six hours without failure during interlamination within a composite structure during formation thereof;
a plurality of electrodes positioned in electrical contact with the piezoelectric material layer;
a plurality of sets of electrode interconnect conductors each positioned in electrical contact with a different subset of the plurality of electrodes and positioned to form a plurality of complementary electrode patterns, each of the plurality of complementary electrode patterns positioned to form an electric field having an electric field axis oriented along a different physical axis from that of an electric field formed by at least one other of the complementary electrode patterns.

11. A piezoelectric planar composite apparatus comprising:
a piezoelectric material;
a first plurality of in-plane electrodes in electrical contact with the piezoelectric material;
a first electrode interconnect conductor carrying layer positioned adjacent the piezoelectric material and carrying a first set of electrode interconnect conductors positioned in electrical contact with the first plurality of electrodes;
a second plurality of in-plane electrodes in electrical contact with the piezoelectric material and positioned in the same plane as the first plurality of electrodes;
a second electrode interconnect conductor carrying layer positioned adjacent the piezoelectric material and carrying a second set of electrode interconnect conductors positioned in electrical contact with a second plurality of electrodes and positioned so that the first electrode interconnect conductor carrying layer is between the piezoelectric material and the second electrode interconnect conductor carrying layer;
a third plurality of in-plane electrodes in electrical contact with the piezoelectric material; and
a third electrode interconnect conductor carrying layer positioned adjacent the piezoelectric material and carrying a third set of electrode interconnect conductors positioned in electrical contact with the third plurality of electrodes, the first, second, and third sets of electrode interconnect conductors positioned to form a plurality of complementary electrode patterns, each of the plurality of complementary electrode patterns positioned to form an electric field having an axis oriented along a different physical axis from that of an electric field formed by at least one other of the complementary electrode patterns.

12. The apparats as defined in claim 11, wherein the second electrode interconnect conductor carrying layer is further positioned so that the second electrode interconnect conductor carrying layer is between the first and the third electrode interconnect conductor carrying layers.

13. The apparatus as defined in claim 11,
wherein the piezoelectric material includes a first and a second side, the second side opposite the first side;
wherein the third electrode interconnect conductor carrying layer is positioned adjacent the first side of the piezoelectric material;
wherein the first and second electrode interconnect conductor carrying layers are positioned adjacent the second side of the piezoelectric material; and
wherein the first electrode interconnect conductor carrying layer is positioned between the second side of the piezoelectric material and the second electrode interconnect conductor carrying layer.

14. The apparatus as defined in claim 11,
wherein the piezoelectric material when operatively positioned includes an axis of usable strain; and
wherein the apparatus is configured so that when operably positioned each of the plurality of complementary electrode patterns are separately selectable by a user to allow the user to select the respective complementary electrode pattern providing an electric field axis most closely matching the axis of usable strain.

15. The apparatus as defined in claim 14, wherein the axis of usable strain varies over time, and wherein the apparatus further comprises a switch positioned to allow the user electrode pattern selection to correspondingly be varied over time.

16. The apparatus as defined in claim 11, wherein the apparatus is configured so that when operably positioned, each of the plurality of complementary electrode patterns are separately selectable by a user to allow the user to align a major piezoelectric polling axis of the apparatus with a separate selected direction of strain.

17. The apparatus as defined in claim 11, wherein the piezoelectric material, each of the electrode interconnect conductor carrying layers, each set of electrode interconnect conductors, and the electrodes are layered on a single substrate.

18. The apparatus as defined in claim 11, further comprising:
an apparatus interconnect layer positioned to connect the apparatus with a carbon fiber structure or carbon epoxy, the interconnect layer comprising an addition-type polyimide resin to enable the piezoelectric planar composite apparatus to withstand a pressure of at least approximately 90 to 100 PSI at a temperature of at least approximately 190° C. for approximately six hours without failure during interlamination within a composite structure during formation thereof.

19. A piezoelectric planar composite apparatus comprising:
a piezoelectric material layer;
a plurality of electrodes positioned in electrical contact with the piezoelectric material layer;
an electrode interconnect conductor carrying layer positioned adjacent the piezoelectric material and carrying a set of electrode interconnect conductors positioned in electrical contact with a subset of the plurality of electrodes;
an apparatus interconnect layer positioned to connect the apparatus with a carbon fiber structure or carbon epoxy, the interconnect layer comprising an addition-type polyimide resin to enable the piezoelectric planar composite apparatus to withstand a high pressure of at least approximately 90 PSI and temperature of at least approximately 160° C. without failure during interlamination within a composite structure during formation thereof.

20. The apparatus as defined in claim 19, wherein the addition-type polyimide resin includes Bismaleimide; and wherein the piezoelectric planar composite apparatus can withstand a pressure of at least approximately 100 PSI and a temperature of at least approximately 190° C. for approximately six hours without failure during interlamination within the composite structure during formation thereof.

21. A piezoelectric planar composite apparatus comprising:
a piezoelectric material layer adapted to be positioned on a structure including an axis of usable strain;
a plurality of electrodes positioned in electrical contact with the piezoelectric material layer and positioned in the same plane to define a plurality of in-plane electrodes, the plurality of in-plane electrodes forming an N×N electrode matrix; and
a plurality of sets of electrode interconnect conductors each positioned in electrical contact with a different subset of the plurality of electrodes and positioned to form a plurality of complementary electrode patterns, each of the plurality of complementary electrode patterns positioned to form an electric field having an electric field axis oriented along a different physical axis from that of an electric field formed by at least one other of the complementary electrode patterns; and
the apparatus being configured so that when operably positioned each of the plurality of complementary electrode patterns are separately selectable by a user to allow the user to select the electrode pattern providing an electric field axis most closely matching the axis of usable strain to thereby enhance power harvesting from the environment by the apparatus.

22. The apparatus as defined in claim 21, wherein the axis of usable strain varies over time, the apparatus further comprising:
a switch positioned to allow user electrode pattern selection to correspondingly be varied over time.

* * * * *